United States Patent [19]

Hewett et al.

[11] Patent Number: 5,405,826
[45] Date of Patent: Apr. 11, 1995

[54] HERBICIDAL PYRIDOPYRIDAZINONES AND PYRIDOPYRIDAZINETHIONES

[75] Inventors: Richard H. Hewett; Simon N. Pettit; Philip H. G. Smith, all of Essex, England

[73] Assignee: Rhone Poulenc Agriculture Limited, Essex, England

[21] Appl. No.: 3,600

[22] Filed: Jan. 13, 1993

[30] Foreign Application Priority Data

Jan. 14, 1992 [GB] United Kingdom ............... 9200689

[51] Int. Cl.$^6$ ............... A01N 43/58; C07D 471/04
[52] U.S. Cl. ............... 504/238; 544/236; 546/315; 558/443
[58] Field of Search ............... 544/236; 514/248; 504/238

[56] References Cited

U.S. PATENT DOCUMENTS

| 4,223,142 | 9/1980 | Denzel et al. | 544/236 |
| 4,881,969 | 11/1989 | Saupe et al. | 504/246 |
| 4,999,044 | 3/1991 | Saupe et al. | 504/237 |
| 4,999,045 | 3/1991 | Saupe et al. | 504/215 |
| 5,204,364 | 4/1993 | Carganico et al. | 514/399 |

FOREIGN PATENT DOCUMENTS

| 0011693 | 6/1980 | European Pat. Off. . |
| 0478195 | 4/1992 | European Pat. Off. . |

(List continued on next page.)

OTHER PUBLICATIONS

Kakimoto et al, *Bull Chem. Soc. Japan*, vol. 40, 153–159 (1967).

(List continued on next page.)

*Primary Examiner*—Emily Bernhardt
*Attorney, Agent, or Firm*—Burns, Doane, Swecker & Mathis

[57] ABSTRACT

Pyrido[2,3-d]pyridazin-5-one and pyrido[2,3-d]pyridazin-5-thione derivatives of general formula (I):

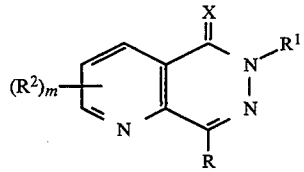

wherein R and $R^1$ independently represent hydrogen, optionally halogenated alkyl, alkenyl or alkynyl, optionally substituted heterocycle or a group —$[CR^{41}R^{42}]_n$-(phenyl)-$(R^3)_q$;

$R^2$ represents halogen, optionally halogenated alkyl, alkenyl or alkynyl, CN; —$CO_2R^4$; —$S(O)_rR^4$; —$NO_2$; —$NR^{41}R^{42}$; —OH; —$COR^4$, —$S(O)_rR^5$, —$CO_2R^5$, —$OR^5$; —$CONR^{41}R^{42}$, —$OSO_2R^5$, —$OSO_2R^6$, —$OCH_2R^5$, —$N(R^{41})COR^6$, —$N(R^{41})SO_2R^5$, —$N(R^{41})SO_2R^6$, —$SO_2NR^{41}R^{42}$, optionally substituted phenyl, alkoxy or haloalkoxy;

X represents oxygen or sulphur;

$R^3$ represents halogen, optionally halogenated alkyl, alkenyl, alkoxy, alkynyl, —OH, —$S(O)_rR^4$, —$CO_2R^4$, $COR^4$, —CN, —$NO_2$, —$NR^{41}R^{42}$, —$OR^5$; —$CONR^{41}R^{42}$, —$OSO_2R^5$, —$OSO_2R^6$, —$OCH_2R^5$, —$N(R^{41})COR^6$, —$N(R^{41})SO_2R^5$, —$N(R^{41})SO_2R^6$ or —$SO_2NR^{41}R^{42}$;

$R^4$ represents a hydrogen atom or optionally halogenated $C_{1-6}$ alkyl;

$R^{41}$ and $R^{42}$, which may be the same or different, each represents a hydrogen atom or optionally halogenated $C_{1-4}$alkyl;

$R^5$ represents a phenyl group optionally substituted by from one to five groups selected from halogen, nitro, cyano, $R^4$ and —$OR^4$;

m represents zero or an integer from one to three;

n represents zero, one or two; where n is two, the groups —$(CR^{41}R^{42})$— may be the same or different;

q represents zero or an integer from one to five; r represents zero, one or two;

with the proviso that when m represents zero R and $R^1$ do not simultaneously represent hydrogen;

and agriculturally acceptable salts thereof are useful as herbicides.

12 Claims, No Drawings

FOREIGN PATENT DOCUMENTS 2184763 12/1973 France .
2708187 8/1978 Germany .
 07146 4/1993 WIPO .

OTHER PUBLICATIONS

*Chemical Abstracts,* vol. 106, 1987, abstract no. 213878m, Yutilov et al.

*Chemical Abstracts,* vol. 104, 1986, abstract no. 207315t, Kaji et al.

Grant & Hackh's *Chemical Dictionary* (5th ed.), p. 564 (1987).

Ohi et al, *Chemical Abstracts,* vol. 115, No. 256193 (1991) (Abstract for WO 012251).

Armarego, *J. Chem. Soc.* p6703 (1963).

Marchand et al, *Bull. Soc. Chem. Fr.* p. 919 (1977).

HERBICIDAL PYRIDOPYRIDAZINONES AND PYRIDOPYRIDAZINETHIONES

This invention relates to novel pyrido[2,3-d]pyridazin-5-ones and pyrido[2,3-d]pyridazin-5-thiones, compositions confining them, processes for their preparation and their use as herbicides. S. Kakimoto and S. Tonooka, Bull. Chem Soc. Japan, Vol. 40, 153-159 (1967) describe the preparation of pyrido[2,3-d]pyridazin-5(6H)-one.

The present invention provides pyrido[2,3-d]pyridazin-5-one and pyrido[2,3-d]pyridazin-5-thione derivatives of general formula (I):

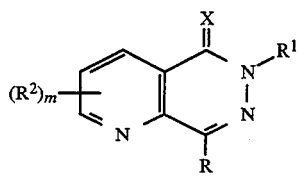

wherein:

R and $R^1$, which may be the same or different, each represents:
a hydrogen atom;
a straight- or branched-chain alkyl, alkenyl or alkynyl group containing up to six carbon atoms optionally substituted by one or more halogen atom;
a group Het; or
a group $—[CR^{41}R^{42}]_n$-(phenyl)-$(R^3)_q$;

$R^2$ represents:
a halogen atom;
a straight- or branched-chain alkyl, alkenyl or alkynyl group containing up to six carbon atoms optionally substituted by one or more halogen atoms;
—CN; —$CO_2R^4$; —$S(O)_rR^4$; —$NO_2$; —$NR^{41}R^{42}$; —OH; —$COR^4$; —$S(O)_rR^5$; —$CO_2R^5$; —$OR^5$; —$CONR^{41}R^{42}$, —$OSO_2R^5$, —$OSO_2R^6$, —$OCH_2R^5$, —$N(R^{41})COR^6$, —$N(R^{41})SO_2R^5$, —$N(R^{41})SO_2R^6$, —$SO_2NR^{41}R^{42}$, a phenyl group optionally substituted by from one to five groups $R^3$;
a straight- or branched-chain alkoxy group containing up to six carbon atoms optionally substituted by one or more halogen atoms;

X represents oxygen or sulphur,
$R^3$ represents:
a halogen atom;
a straight- or branched-chain alkoxy group containing up to six carbon atoms optionally substituted by one or more halogen atoms;
a straight- or branched-chain alkyl, alkenyl or alkynyl group containing up to six carbon atoms optionally substituted by one or more halogen atoms; —OH; —$S(O)_rR^4$; —$CO_2R^4$; —$COR^4$; —CN; —$NO_2$; —$NR^{41}R^{42}$; —$S(O)_rR^5$; —$CO_2R^5$; —$OR^5$; —$CONR^{41}R^{42}$, —$OSO_2R^5$, —$OSO_2R^6$, —$OCH_2R^5$, —$N(R^{41})COR^6$, —$N(R^{41})SO_2R^5$, —$N(R^{41})SO_2R^6$, or —$SO_2NR^{41}R^{42}$;

$R^4$ represents a hydrogen atom or a straight- or branched-chain alkyl group containing up to six carbon atoms optionally substituted by one or more halogen atoms;

$R^{41}$ and $R^{42}$, which may be the same or different, each represents a hydrogen atom or a straight- or branched-chain alkyl group containing up to four carbon atoms optionally substituted by one or more halogen atoms;

$R^5$ represents a phenyl group optionally substituted by from one to five groups selected from halogen, nitro, cyano, $R^4$ and —$OR^4$;

$R^6$ represents a straight- or branched-chain alkyl group containing up to six carbon atoms optionally substituted by one or more halogen atoms;

Het represents a 5 or 6 membered heterocycle containing from 3 to 5 carbon atoms in the ring and one or more heteroatoms in the ring selected from nitrogen, oxygen and sulphur, e.g. pyridyl, pyrimidinyl, thienyl, piperidyl or pyrazolyl; optionally substituted by one or more groups $R^3$;

m represents zero or an integer from one to three; where m is greater than one the groups $R^2$ may be the same or different;

n represents zero, one or two; where n is two, the groups $—(CR^{41}R^{42})—$ may be the same or different;

q represents zero or an integer from one to five; where q is greater than one the groups $R^3$ may be the same or different;

r represents zero, one or two;

with the proviso that when m represents zero R and $R^1$ do not simultaneously represent hydrogen;
and agriculturally acceptable salts thereof.

Compounds in which X represents oxygen and $R^1$ represents hydrogen may exist in enolic tautomeric forms. Furthermore, in certain cases, the substituents R, $R^1$, $R^2$, $R^3$, $R^4$, $R^{41}$, $R^{42}$, $R^5$ and $R^6$ contribute to optical and/or stereoisomerism. All such forms are embraced by the present invention.

Compounds of formula I in which R, $R^1$ and $R^2$ simultaneously represent hydrogen are not considered part of the invention but compositions containing them and their use as herbicides are considered as a pan of the invention.

By the term "agriculturally acceptable salts" is meant salts the cations or anions of which are known and accepted in the art for the formation of salts for agricultural or horticultural use. Preferably the salts are water soluble. Suitable salts formed by compounds of formula I which are acidic, e.g. compounds containing a carboxy group, with bases include alkali metal (e.g. sodium and potassium) salts, alkaline earth metal (e.g. calcium and magnesium) salts and ammonium (e.g. diethanolamine, triethanolamine, octylamine, dioctylamine and morpholine) salts.

Suitable acid addition salts, formed by compounds of formula I containing an amino group, include salts with inorganic acids, for example hydrochlorides, sulphates, phosphates and nitrates and salts with organic acids, for example acetic acid.

It is to be understood that where reference is made in the specification to the compounds of formula I, such reference is intended to include salts where the context so permits.

A preferred class of compounds of general formula I because of their herbicidal activity are those wherein
$R^2$ represents:
a halogen atom; or
a straight- or branched-chain alkyl, alkenyl or alkynyl group containing up to six carbon atoms optionally substituted by one or more halogen atoms;

—CN; —CO$_2$R$^4$; —S(O)$_r$R$^4$; —NO$_2$; —NR$^{41}$R$^{42}$; —OH; —COR$^4$; a phenyl group optionally substituted by from one to five groups R$^3$; or a straight- or branched-chain alkoxy group containing up to six carbon atoms optionally substituted by one or more halogen atoms;

R$^3$ represents:
 a halogen atom;
 a straight- or branched-chain alkoxy group containing up to six carbon atoms optionally substituted by one or more halogen atoms;
 a straight- or branched-chain alkyl, alkenyl or alkynyl group containing up to six carbon atoms optionally substituted by one or more halogen atoms;
 —OH; —S(O)$_r$R$^4$; —CO$_2$R$^4$; —COR$^4$; —CN; —NO$_2$; —NR$^{41}$R$^{42}$.

A further preferred class of compounds of formula I are those wherein:
 R and R$^1$, which may be the same or different, each represents a phenyl group optionally substituted by one or more groups R$^3$; and
 R$^2$ represents a halogen atom;
 a straight- or branched-chain alkyl group containing up to 4 carbon atoms;
 —CO$_2$R$^4$ or —CF$_3$.

A particularly preferred class of compounds of formula I because of their herbicidal activity are those having one or more of the following features:
 R and R$^1$, which may be the same or different, each represents a phenyl group optionally substituted by one or more groups R$^3$;
 m represents zero;
 X represents oxygen.

A further preferred class of compounds of formula I are those wherein
 R and R$^1$, which may be the same or different, each represent a phenyl group which is:
  unsubstituted; or
  mono-substituted in the 3- or 4-position by a group R$^3$; or
  di-substituted in the 2- and 4-position by two groups R$^3$ which may be the same or different.

A particularly preferred class of compounds of formula I are those wherein R and R$^1$, which may be the same or different, each represent a phenyl group which is disubstituted in the 3- and 4-positions by two groups R$^3$.

Compounds in which R$^2$ represents an alkyl group, preferably methyl are also preferred.

Preferably the 3-position of the pyrido[2,3-d]pyridazin-5-one or -5-thione derivative of formula I is substituted by a group R$^2$.

Particularly preferred compounds because of their herbicidal activity include the following:
1. 6,8-Diphenylpyrido[2,3-d]pyridazin-5-one;
2. 6-Phenyl-8-(3-trifluoromethylphenyl)pyrido[2,3-d]pyridazin-5-one;
3. 6-(4-Fluorophenyl)-8-(3-trifluoromethylphenyl)pyrido[2,3-d]pyridazin-5-one;
4. 6-(2,4-Difluorophenyl)-8-(3-trifluoromethylphenyl)pyrido[2,3-d]pyridazin-5-one;
5. 6-(4-Fluorophenyl)-8-(3-methoxyphenyl)pyrido[2,3-d]pyridazin-5-one;
6. 6-(4-Methoxyphenyl)-8-(3-trifluoromethylphenyl)pyrido[2,3-d]pyridazin-5-one;
7. 6-(4-Chlorophenyl)-8-(3-trifluoromethylphenyl)pyrido[2,3-d]pyridazin-5-one;
8. 8-(3-Chlorophenyl)-6-(4-fluorophenyl)pyrido[2,3-d]pyridazin-5-one;
9. 6-(4-Methylphenyl)-8-(3-trifluoromethylphenyl)pyrido[2,3-d]pyridazin-5-one;
10. 8-(4-Chlorophenyl)-6-(4-fluorophenyl)pyrido[2,3-d]pyridazin-5-one;
11. 6-(4-Fluorophenyl)-8-phenylpyrido[2,3-d]pyridazin-5-one;
12. 8-(3-Cyanophenyl)-6-(4-fluorophenyl)pyrido[2,3-d]pyridazin-5-one;
13. 8-(2-Chlorophenyl)-6-(4-fluorophenyl)pyrido[2,3-d]pyridazin-5-one;
14. 6-(4-Fluorophenyl)-8-(3-trifluoromethylphenyl)pyrido[2,3-d]pyridazin-5-thione;
15. 6-(4-Fluorophenyl)-3-methyl-8-(3-trifluoromethylphenyl)pyrido[2,3-d]pyridazine-5-one;
16. 6-(3-Fluorophenyl)-8-(3-trifluoromethylphenyl)pyrido[2,3-d]pyridazin-5-one;
17. 8-(3-Trifluoromethylphenyl)-6-(4-trifluoromethylphenyl)pyrido[2,3-d]pyridazin-5-one;
18. 6-(4-Fluorophenyl)-2-methyl-8-(3-trifluoromethylphenyl)pyrido[2,3-d]pyridazin-5-one;
19. 6-(4-Methanesulphonylphenyl)-8-(3-trifluoromethylphenyl)pyrido[2,3-d]pyridazin-5-one;
20. 6-(4-Bromophenyl)-8-(3-trifluoromethylphenyl)pyrido[2,3-d]pyridazin-5-one;
21. 6-(3-Methylphenyl)-8-(3-trithoromethylphenyl)pyrido[2,3-d]pyridazin-5-one;
22. 6-(3,4-Dichlorophenyl)-8-(3-trifluoromethylphenyl)pyrido[2,3-d]pyridazin-5-one;
23. 6-(Pyrid-2-yl)-8-(3-trifluoromethylphenyl)pyrido[2,3-d]pyridazin-5-one;
24. 8-(3-Trifluoromethylphenyl)pyrido[2,3-d]pyridazin-5-(6H)-one;
25. 6-(3-Cyanophenyl)-8-(3-trifluoromethylphenyl)pyrido[2,3-d]pyridazin-5-one;
26. 6-Methyl-8-(3-trifluoromethylphenyl)pyrido-[2,3-d]pyridazin-5-one;
27. 6-(4-Fluorophenyl)-8-(3-trifluoromethoxyphenyl)pyrido[2,3-d]pyridazin-5-one;
28. 6-(3,4-Difluorophenyl)-8-(3-trifluoromethylphenyl)pyrido[2,3-d]pyridazin-5-one;
29. 8-(3-Bromophenyl)-6-(4-fluorophenyl)pyrido-[2,3-d]pyridazin-5-one;
30. 3-Methyl-8-(3-trifluoromethylphenyl)pyrido[2,3-d]pyridazin-5-(6H)-one;
31. 8-(3-Cyanophenyl)-6-(4-trifluoromethylphenyl)pyrido[2,3-d]pyridazin-5-one;
32. 6-(4-Chlorophenyl)-8-(3-cyanophenyl)pyrido-[2,3-d]pyridazin-5-one;
33. 6-(4-Fluorophenyl)-8-[(3-methylthio)phenyl]pyrido-[2,3-d]pyridazin-5-one;
34. 6-(4-Fluorophenyl)-8-(3-methanesulphonylphenyl)pyrido[2,3-d]pyridazin-5-one;
35. 6-(4-Chlorophenyl)-3-methyl-8-(3-trifluoromethylphenyl)pyrido[2,3-d]pyridazin-5-one;
36. 3-Methyl-6-(4-trifluoromethylphenyl)-8-(3-trifluoromethylphenyl)pyrido[2,3-d]pyridazin-5-one;
37. 6-(4-Chlorophenyl)-8-(3-trifluoromethoxyphenyl)pyrido[2,3-d]pyridazin-5-one;
38. 8-(3-Trifluoromethoxyphenyl)-6-(4-trifluoromethylphenyl)pyrido[2,3-d]pyridazin-5-one;
39. 6-(4-Chlorophenyl)-3-methyl-8-(3-trifluoromethoxyphenyl)pyrido[2,3-d]pyridazin-5-one;
40. 3-Methyl-8-(3-trifluoromethoxyphenyl)-6-(4-trifluoromethylphenyl)pyrido[2,3-d]pyridazin-5-one;

41. 6-(4-Fluorophenyl)-3-methyl-8-(3-trifluoromethoxyphenyl)pyrido[2,3-d]pyridazin-5-one;
42. 8-(3-Cyanophenyl)-6-(4-fluorophenyl)-3-methylpyrido[2,3-d]pyridazin-5-one;
43. 6-(4-Trifluoromethoxyphenyl)-8-(3-trifluoromethylphenyl)pyrido[2,3-d]pyridazin-5-one;
44. 6-(3-Trifluoromethylphenyl)-8-(3-trifluoromethylphenyl)pyrido[2,3-d]pyridazin-5-one;
45. 6-(4-Nitrophenyl)-8-(3-trifluoromethylphenyl)pyrido[2,3-d]pyridazin-5-one;
46. 8-(3-Cyanophenyl)-3-methyl-6-(4-trifluoromethylphenyl)pyrido[2,3-d]pyridazin-5-one;
47. 6-(4-Aminophenyl)-8-(3-trifluoromethylphenyl)pyrido[2,3-d]pyridazin-5-one;
48. 6-(4-Fluorophenyl)-8-(3-methylphenyl)pyrido[2,3-d]pyridazin-5-one;
49. 6-(4-Fluorophenyl)-3-propyl-8-(3-trifluoromethylphenyl)pyrido-[2,3-d]pyridazin-5-one;
50. 6-(2-Chloro-4-trifluoromethylphenyl)-8-(3-trifluoromethylphenyl)pyrido[2,3-d]pyridazin-5-one;
51. 6-(4-Aminosulphonylphenyl)-8-(3-trifluoromethylphenyl)pyrido-[2,3-d]pyridazin-5-one;
52. 6-(3-Nitrophenyl)-8-(3-trifluoromethylphenyl)pyrido-[2,3-d]pyridazin-5-one.

The numbers 1 to 52 are assigned to these compounds for reference and identification hereinafter.

Compounds of general formula I may be prepared by the application or adaptation of known methods (i.e. methods heretofore used or described in the literature), for example as hereinafter described.

In the following description, where symbols appearing in formulae are not specifically defined, it is to be understood that they are "as hereinbefore defined" in accordance with the first definition of each symbol in the specification.

It is to be understood that in the description of the following processes the sequences may be performed in different orders, and that suitable protecting groups may be required to achieve the compounds sought.

According to a feature of the present invention compounds of general formula I wherein X represents oxygen may be prepared by the reaction of a compound of formula II with a hydrazine of formula III or a salt thereof:

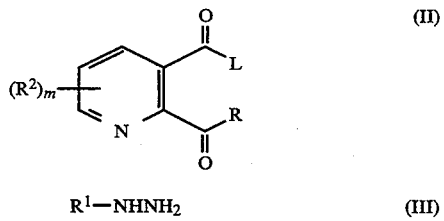

$R^1$—NHNH$_2$ (III)

wherein L is a leaving group. Generally L is OH, straight- or branched-chain alkoxy containing up to 4 carbon atoms (e.g. ethoxy), or halogen, for example chlorine. The reaction is generally carried out in a solvent such as toluene or ethanol. Where the hydrazine of formula III is used in the form of a salt (such as the hydrochloride) the reaction is generally performed in the presence of a base or acid acceptor such as triethylamine or potassium carbonate. The reaction is generally performed from room temperature to the reflux temperature of the mixture and preferably with azeotropic removal of water from the mixture.

According to a further feature of the present invention compounds of formula I in which X represents oxygen may be prepared by the cyclisation of a compound of formula (IIa):

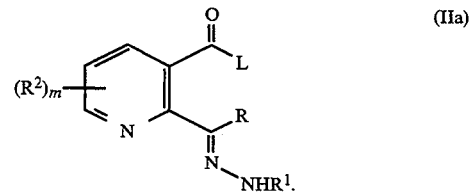

The reaction is generally carried out in an alcoholic solvent such as methanol or ethanol in the presence of a base or acid acceptor such as triethylamine or potassium carbonate optionally in the presence of a catalyst, for example para-toluenesulphonic acid. The reaction is generally performed at a temperature from room temperature to the reflux temperature of the mixture and preferably with azeotropic removal of water from the mixture.

According to a further feature of the present invention compounds of formula I wherein X represents sulphur may be prepared from corresponding compounds of formula I in which X represents oxygen by reaction with a thionation reagent to convert the carbonyl group to a thiocarbonyl group. Suitable thionation reagents include Lawessons' Reagent, i.e. [2,4-bis(4-methoxyphenyl)-1,3-dithia-2,4-diphosphetane-2,4-disulphide], and phosphorus pentasulphide. The reaction is generally carried out in a suitable solvent, for example toluene, at a temperature from 50° C. to the reflux temperature of the mixture.

Compounds of formula II where L is OH or straight- or branched-chain alkoxy containing up to 4 carbon atoms may be prepared by the oxidation of compounds of formula IV:

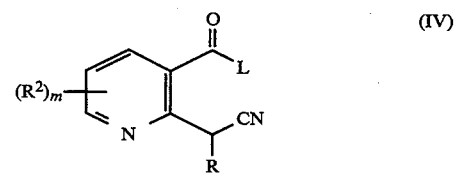

to convert the cyano-methylene group to a carbonyl group. The reaction is carried out in the presence of a base, for example lithium diisopropylamide, potassium carbonate or sodium hydride, in an anhydrous solvent, for example dimethyl sulphoxide, tetrahydrofuran (THF) or acetonitrile at temperatures from −72° C. to the reflux temperature of the mixture. Generally the oxidant used is air or oxygen.

Alternatively, the reaction may be carried out in a two-phase system comprising an organic solvent such as toluene or dichloromethane and an aqueous solution of a base, for example sodium hydroxide, in the presence of a quaternary ammonium salt, for example triethyl benzylammonium chloride. Generally the oxidant used is air or oxygen. The reaction is generally performed at a temperature from room temperature to the reflux temperature of the mixture.

Compounds of formula II where L is straight- or branched-chain alkoxy containing up to 4 carbon atoms and R is hydrogen may also be prepared by the reduction of the corresponding pyridine dicarboxylates in which R is replaced by OH, for example as described by Queguiner et at., Bull. Soc. Chim. Fr., 1969, 3678.

Compounds of formula H in which L is straight- or branched-chain alkoxy containing up to 4 carbon atoms, or halogen may be prepared from the corresponding carboxylic acid of formula II in which L represents —OH by the application or modification of known methods.

Compounds of formula IIa may be prepared by the reaction of a compound of formula II with a compound of formula III or a salt thereof. The reaction is generally performed in a solvent such as ethanol or methanol optionally in the presence of a base, for example triethylamine or potassium carbonate (the presence of a base is particularly preferred where a salt of formula III is used) and a catalyst, for example para-toluenesulphonic acid. The reaction is generally carried out at a temperature from ambient to the reflux temperature of the solvent.

Compounds of formula IV in which L is straight- or branched-chain alkoxy containing up to 4 carbon atoms, or preferably OH may be prepared by the reaction between a nicotinic acid derivative of formula V and a nitrile of general formula VI:

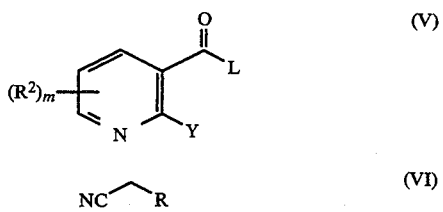

(V)

(VI)

wherein Y is a leaving group, for example halogen. The reaction is performed in the presence of a base, for example sodium hydride, sodium amide or an alkali metal alkoxide in a solvent, for example toluene, 1,4-dioxane or THF, at temperatures between 0° C. and the reflux temperature of the solvent. The reaction is optionally performed in the presence of a phase transfer catalyst, for example tris[2-(2-methoxyethoxy)ethyl]amine (commonly known as TDA-1).

Compounds of formula IV in which R represents a straight- or branched-chain alkyl, alkenyl or alkynyl group containing up to six carbon atoms optionally substituted by one or more halogen atoms, or a group —[CR$^{41}$R$^{42}$]$_n$-(phenyl)-(R$^3$)$_q$ wherein n is one or two, may be prepared by the reaction of a 2-cyanomethylnicotinic acid derivative of formula VII with a compound of general formula VIII:

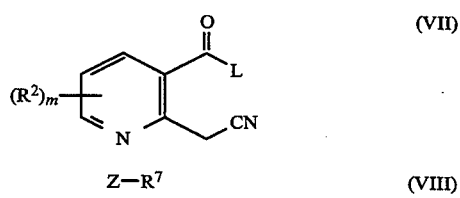

(VII)

(VIII)

wherein L is —OH or straight- or branched-chain alkoxy containing up to 4 carbon atoms and R$^7$ represents a straight- or branched-chain alkyl, alkenyl or alkynyl group containing up to six carbon atoms optionally substituted by one or more halogen atoms, or a group —[CR$^{41}$R$^{42}$]$_n$-(phenyl)-(R$^3$)$_q$ wherein n is one or two, and Z is a leaving group, for example halogen or tosyl. The reaction is performed in the presence of a base and is widely described in the chemical literature (for example, as described by Masuyama et al., Chem. Lett., 1977, 1439).

Compounds of formula VII where L is OH or alkoxy may be prepared by the cyanation of a compound of formula IX:

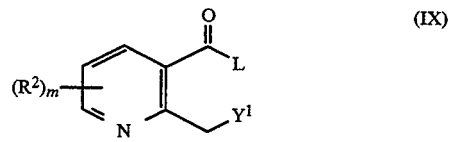

(IX)

wherein Y$^1$ is a leaving group, for example chlorine or bromine and the cyanide source is, for example sodium cyanide. The reaction is conducted in a solvent, for example aqueous ethanol at a temperature between room temperature and the reflux temperature of the solvent mixture.

Compounds of formula IX in which Y$^1$ represents a halogen atom, for example a chlorine or bromine atom, may be prepared by the halogenation of a methylpyridine compound of formula X:

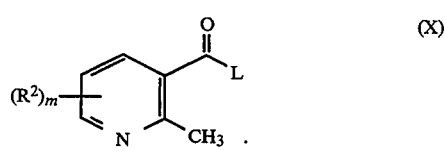

(X)

The reaction is performed in the presence of a suitable halogen source, for example N-chloro- or N-bromosuccinimide in a solvent, for example carbon tetrachloride or chloroform at a temperature between room temperature and the reflux temperature of the solvent. The reaction is preferably conducted in the presence of a reaction initiator, for example benzoyl peroxide.

The hydrazines of formula III, the nitriles of formula VI and the compounds of formulae V, VIII and X are known or may be prepared by the application or modification of known methods.

The following Examples illustrate the preparation of compounds of the general formula I and the Reference Examples illustrate the preparation of intermediates. In the present specification m.p. means melting point. Unless otherwise stated percentages are by weight.

Example 1

Compounds 1, 2, 48, 49, 51 and 52

Preparation of 6,8-diphenylpyrido[2,3-d]pyridazin-5-one

A mixture of phenylhydrazine (5.0 g) and 2-benzoylnicotinic acid (3.25 g) in toluene was stirred at the reflux temperature for 7 hours. The solvent was then evaporated and the residue was purified by chromatography to give the crude product which, on trituration with diethyl ether, yielded the title compound as a yellow solid, 0.41 g, m.p. 173.5°–176.5° C.

By proceeding in a similar manner the following compounds of general formula I were prepared:

2. 6-Phenyl-8-(3-trifluoromethylphenyl)pyrido[2,3-d]pyridazin-5-one, m.p. 118°–123° C.

48. 6-(4-Fluorophenyl)-8-(3-methylphenyl)pyrido[2,3-d]pyridazin-5-one; m.p. 162°–163° C.

49. 6-(4-Fluorophenyl)-3-propyl-8-(3-trifluoromethylphenyl)pyrido[2,3-d]pyridazin-5-one; m.p. 103.5°–104.5° C.

51. 6-(4-Aminosulphonylphenyl)-8-(3-trifluoromethylphenyl)pyrido[2,3-d]pyridazin-5-one; m.p. 234°–236° C.

52. 6-(3-Nitrophenyl)-8-(3-trifluoromethylphenyl)pyrido[2,3-d]pyridazin-5-one; m.p. 221.5°–223.5° C.

Example 2

Compound 3-13, 15, 16, 18, 20–23, 27, 29, 32, 33, 35, 37, 39, 41–43

Preparation of 6-(4-fluorophenyl-8-(3-trifluoromethylphenyl)pyrido[2,3-d]pyridazin-5-one.

Triethylamine (2.1 g) was added to a mixture of 2-(3-trifluoromethylbenzoyl)nicotinic acid (3.3 g) and 4-fluorophenylhydrazine hydrochloride (3.25 g) in toluene. The mixture was stirred at the reflux temperature for 2.5 hours, water was removed azeotropically from the mixture using a Dean-Stark apparatus. The precipitated triethylamine hydrochloride was removed by filtration. The filtrate was washed successively with 0.5N hydrochloric acid then brine. The organic phase was dried and then evaporated. The crude product was triturated with diethyl ether to yield the title compound as a colourless solid, 2.2 g, m.p. 155°–158° C.

By proceeding in a similar manner, the following compounds of general formula I were prepared from the corresponding 2-benzoylnicotinic acids:

4. 6-(2,4-Difluorophenyl)-8-(3-trifluoromethylphenyl)pyrido[2,3-d]pyridazin-5-one, m.p. 124°–126° C.

5. 6-(4-Fluorophenyl)-8-(3-methoxyphenyl)pyrido[2,3-d]pyridazin-5-one, m.p. 163°–164° C.

6. 6-(4-Methoxyphenyl)-8-(3-trifluoromethylphenyl)pyrido[2,3-d]pyridazin-5-one, m.p. 146°–148° C.

7. 6-(4-Chlorophenyl)-8-(3-trifluoromethylphenyl)pyrido[2,3-d]pyridazin-5-one, m.p. 100°–102° C.

8. 8-(3-Chlorophenyl)-6-(4-fluorophenyl)pyrido[2,3-d]pyridazin-5-one, m.p. 180°–181° C.

9. 6-(4-Methylphenyl)-8-(3-trifluoromethylphenyl)pyrido[2,3-d]pyridazin-5-one, m.p. 167.5°–168.5° C.

10. 8-(4-Chlorophenyl)-6-(4-fluorophenyl)pyrido[2,3-d]pyridazin-5-one, m.p. 202°–203° C.

11. 6-(4-Fluorophenyl)-8-phenylpyrido[2,3-d]pyridazin-5-one, m.p. 171°–173° C.

12. 8-(3-Cyanophenyl)-6-(4-fluorophenyl)pyrido[2,3-d]pyridazin-5-one; m.p. 218°–220° C.

13. 8-(2-Chlorophenyl)-6-(4-fluorophenyl)pyrido[2,3-d]pyridazin-5-one; m.p. 173°–175° C.

15. 6-(4-Fluorophenyl)-3-methyl-8-(3-trifluoromethylphenyl)pyrido[2,3-d]pyridazine-5-one; m.p. 146°–158° C.

16. 6-(3-Fluorophenyl)-8-(3-trifluoromethylphenyl)pyrido-[2,3-d]pyridazin-5-one; m.p. 129°–131° C.

18. 6-(4-Fluorophenyl)-2-methyl-8-(3-trifluoromethylphenyl)pyrido[2,3-d]pyridazin-5-one; m.p. 153.1°–155.5° C.

20. 6-(4-Bromophenyl)-8-(3-trifluoromethylphenyl)pyrido[2,3-d]pyridazin-5-one; m.p. 134°–136° C.

21. 6-(3-Methylphenyl)-8-(3-trifluoromethylphenyl)pyrido[2,3-d]pyridazin-5-one; m.p. 117.5°–119.5° C.

22. 6-(3,4-Dichlorophenyl)-8-(3-trifluoromethylphenyl)pyrido[2,3-d]pyridazin-5-one; m.p. 150°–151° C.

23. 6-(Pyrid-2-yl)-8-(3-trifluoromethylphenyl)pyrido[2,3-d]pyridazin-5-one; m.p. 196°–199° C.

27. 6-(4-Fluorophenyl)-8-(3-trifluoromethoxyphenyl)pyrido[2,3-d]pyridazin-5-one; m.p. 129°–131° C.

29. 8-(3-Bromophenyl)-6-(4-fluorophenyl)pyrido[2,3-d]pyridazin-5-one; m.p. 186°–187.5° C.

32. 6-(4-Chlorophenyl)-8-(3-cyanophenyl)pyrido[2,3-d]pyridazin-5-one; m.p. 240°–241° C.

33. 6-(4-Fluorophenyl)-8-[(3-methylthio)phenyl]pyrido[2,3-d]pyridazin-5-one; m.p. 119°–121° C.

35. 6-(4-Chlorophenyl)-3-methyl-8-(3-trifluoromethylphenyl)pyrido[2,3-d]pyridazin-5-one; m.p. 150°–153° C.

37. 6-(-4-Chlorophenyl)-8-(3-trifluoromethoxyphenyl)pyrido[2,3-d]pyridazin-5-one; m.p. 100°–101° C.

39. 6-(4-Chlorophenyl)-3-methyl-8-(3-trifluoromethoxyphenyl)pyrido[2,3-d]pyridazin-5-one; m.p. 135°–136° C.

41. 6-(4-Fluorophenyl)-3-methyl-8-(3-trifluoromethoxyphenyl)pyrido[2,3-d]pyridazin-5-one; m.p. 126°–128° C.

42. 8-(3-Cyanophenyl)-6-(4-fluorophenyl)-3-methylpyrido[2,3-d]pyridazin-5-one; m.p. 255°–256° C.

43. 6-(4-Trifluoromethoxyphenyl)-8-(3-trifluoromethylphenyl)pyrido[2,3-d]pyridazin-5-one; m.p. 107°–108° C.

Example 3

Compounds 17, 19, 25, 28, 31, 36, 38, 40, 44–46, 50

Preparation of 8-(3-trifluoromethylphenyl)-6-(4-trifluoromethylphenyl)pyrido[2,3-d]pyridazin-5-one A suspension of 2-(3-trifluoromethylbenzoyl)nicotinic acid (1.5 g) and 4-trifluoromethylphenylhydrazine (1.34 g) in toluene was stirred at reflux temperature for 3 hours (water was removed azeotropically from the mixture).

The resulting solution was washed successively with 2N hydrochloric acid then water. The organic phase was dried and then evaporated. The crude product was triturated in diethyl ether to yield the title compound as a beige solid, 0.72 g, m.p. 129°–131° C.

By proceeding in a similar manner, the following compounds of general formula I were prepared:

| Compd. | Compound | m.p. |
|---|---|---|
| 19 | 6-(4-Methanesulphonylphenyl)-8-(3-trifluoromethylphenyl)pyrido[2,3-d]pyridazin-5-one; | 218.5–221° C. |
| 25 | 6-(3-Cyanophenyl)-8-(3-trifluoromethylphenyl)pyrido-[2,3-d]pyridazin-5-one; | 185–186° C. |
| 28 | 6-(3,4-Difluorophenyl)-8-(3-trifluoromethylphenyl)-pyrido-[2,3-d]pyridazin-5-one; | 125.5–127° C. |
| 31 | 8-(3-Cyanophenyl)-6-(4-trifluoromethylphenyl)pyrido-[2,3-d]pyridazin-5-one; | 203–206° C. |
| 36 | 3-Methyl-6-(4-trifluoromethylphenyl)-8-(3-trifluoromethylphenyl)-pyrido[2,3-d]pyridazin-5-one; | 134.5–136° C. |
| 38 | 8-(3-Trifluoromethoxyphenyl)-6-(4-trifluoromethylphenyl)-pyrido[2,3-d]pyridazin-5-one; | 104–106° C. |
| 40 | 3-Methyl-8-(3-trifluoromethoxyphenyl)-6-(4-trifluoromethylphenyl)pyrido[2,3-d]pyridazin-5-one; | 132.5–140° C. |
| 44 | 6-(3-Trifluoromethylphenyl)-8-(3-trifluoromethylphenyl)pyrido[2,3-d]pyridazin-5-one; | 119–122° C. |
| 45 | 6-(4-Nitrophenyl)-8-(3-trifluoromethylphenyl)pyrido-[2,3-d]pyridazin-5-one; | 169–170° C. |
| 46 | 8-(3-Cyanophenyl)-3-methyl-6-(4-trifluoromethyl-phenyl)- | 237–239° C. |

| Compd. | Compound | m.p. |
|---|---|---|
| 50 | pyrido[2,3-d]pyridazin-5-one;<br>6-(2-Chloro-4-trifluoromethylphenyl)<br>-8-(3-trifluoromethylphenyl)pyrido<br>[2,3-d]pyridazin-5-one. | 127–129° C. |

Example 4

Compound 14

Preparation of 6-(4-Fluorophenyl)-8-(3-trifluoromethylphenyl)pyrido[2,3-d]pyridazin-5-thione A suspension of 6-(4-fluorophenyl)-8-(3-trifluoromethylphenyl)pyrido[2,3-d]pyridazin-5-one (2.4 g) and Lawessons' Reagent (1.49 g) in toluene was stirred at 80°–85° C. under an inert atmosphere for 5 hours. The solvent was evaporated and the residue was purified by chromatography to yield the title compound as a yellow solid, 0.45 g, m.p. 214°–215° C.

Example 5

Compound 24 and 26

Preparation of 8-(3-Trifluoromethylphenyl)pyrido[2,3-d]pyridazin-5-(6H)-one.

A mixture of 2-(3-trifluoromethylbenzoyl)nicotinic acid (1.5 g) and hydrazine hydrate (0.4 g) in ethanol was heated at the reflux temperature for 5 hours. On cooling and reduction of the volume of solvent by evaporation, a precipitate formed which was collected by filtration, to give the title compound as a white solid, 1.08 g, m.p. 210°–215° C.

By proceeding in a similar manner but replacing hydrazine with methylhydrazine, Compound 26 was prepared:

6-Methyl-8-(3-trifluoromethylphenyl)pyrido[2,3-d]pyridazin-5-one; m.p. 167.5°–168.5° C.

Example 6

Compound 30

Preproration of 3-methyl-8-(3-trifluoromethylphenyl)-pyrido[2,3-d]pyridazin-5-(6H)-one.

A solution of sodium dichromate (1.2 g) in water (1 ml) was added to an ice-cooled solution of 6-(4-fluorophenyl)-3-methyl-8-(3-trifluoromethylphenyl)-pyrido[2,3-d]pyridazin-5-one (1.0 g) in 80% sulphuric acid (3 ml). An exotherm occurred and the reaction temperature rose to 80° C. The mixture was stirred for 2 hours at room temperature and then diluted with water and extracted with ethyl acetate. The organic phase was dried then evaporated. The crude product was purified by column chromatography to field the title compound as a white solid, 0.2 g, m.p. 207.5°–209.5° C.

Example 7

Compound 34

The preparation of 6-(4-fluorophenyl)-8-(3-methylsulphonylphenyl)pyrido[2,3-d]pyridazin-5-one A solution of monoperoxyphthalic acid magnesium salt (1.09 g) in water was added to a stirred suspension of 6-(4-fluorophenyl)-8-(3-methylthiophenyl)-pyrido[2,3-d]pyridazin-5-one (1.3 g) in ethanol at 29°–33° C. A further quantity of 50% ethanol:water mixture was added to the paste mixture. The resulting mixture was stirred at 45°–50° C. for 1.75 hours. The mixture was cooled to 35° C. and a solution of monoperoxyphthalic acid (1.3 g) in water was added. The mixture was stirred at 45°–50° C. for a further 2.75 hours then allowed to stand at room temperature overnight.

After the solvent was evaporated the residue was partitioned between ethyl acetate and water. The organic layer was washed with water, dried and evaporated.

The crude product was purified by column chromatography to yield the title compound as a white solid, 0.73 g, m.p. 168.5°–170.5° C.

Example 8

Compound 47

The preparation of 6-(4-aminophenyl)-8-(3-trifluoromethylphenyl)pyrido[2,3-d]pyridazin-5-one Tin (II) chloride dihydrate (1.56 g) was dissolved in ethanol (4 ml) and concentrated hydrochloric acid (2 ml). The cloudy solution was stirred at room temperature for 10 minutes. 6-(4-Nitrophenyl)-8-(3-trifluoromethylphenyl)pyrido[2,3-d]pyridazin-5-one (1.0 g) was then added portionwise to the stirred solution. The resulting suspension was stirred at room temperature for 24 hours. A further 0.5 g of the tin (II) dichloride dihydrate was added. Stirring was continued for a further 5.5 hours. Solvent was evaporated. The residue was diluted with a small amount of water, basified to pH 10 with 2N sodium hydroxide solution then extracted with ethyl acetate. The organic extracts were combined, washed with water, dried and evaporated. The crude product was triturated with cyclohexane/diethyl ether mixture to yield the title compound as a yellow solid, 0.72 g, m.p. 155°–157° C.

Reference Example 1

Preparation of 2-benzoylnicotinic acid.

A solution of phenylacetonitrile (3.16 g) in dry 1,4-dioxane was added to a stirred suspension of sodium hydride (60% as an oil suspension, 3.25 g) in dry 1,4-dioxane. The resulting suspension was stirred at ambient temperature for 5 minutes. A solution of 2-chloronicotinic acid (4.0 g) in dry 1,4-dioxane was then added. The reaction mixture was then stirred at the reflux temperature for 3 hours. The orange suspension was allowed to cool to 80° C. and air was then passed through the stirred mixture for 3 hours whilst maintaining the temperature at 65° C.

The resulting green suspension was poured into water and washed with diethyl ether. The aqueous phase was separated and acidified to pH 3 with 2N hydrochloric acid. The mixture was extracted with ethyl acetate. The combined organic extracts were washed with water, dried and evaporated. The resulting solid was triturated in diethyl ether, filtered and dried to yield the title compound as a yellow solid, 3.13 g, m.p. 171°–176° C.

By proceeding in a similar manner, the following compounds of general formula II were prepared:

i) 2-(3-Chlorobenzoyl)nicotinic acid, m.p. 204°–205° C.

ii) 2-(4-Chlorobenzoyl)nicotinic acid, m.p. 169°–175° C.

iii) 2-(3-Methoxybenzoyl)nicotinic acid, m.p. 115°–121° C.

iv) 2-(3-Trifluoromethylbenzoyl)nicotinic acid, m.p. 200° C. (with decomposition).

v) 2-(3-Cyanobenzoyl)nicotinic acid, m.p. 160°–164° C.

vi) 2-(2-Chlorobenzoyl)nicotinic acid, m.p. 146°–150° C.

vii) 6-Methyl-2-(3-trifluoromethylbenzoyl)nicotinic acid, m.p. 162°–164° C.

viii) 2-(3-Trifluoromethoxybenzoyl)nicotinic acid, m.p. 147°–150° C.

ix) 2-(3-Bromobenzoyl)nicotinic acid, m.p. 202°–203.5° C.

x) 5-Methyl-2-(3-trifluoromethylbenzoyl)nicotinic acid, m.p. 165°–167° C.

xi) 2-(3-Methylthiobenzoyl)nicotinic acid, m.p. 151°–154° C.

xii) 5-Methyl-2-(3-trifluoromethoxybenzoyl)nicotinic acid, m.p. 134°–138° C.

Reference Example 2

The preparation of 2-(3-methylbenzoyl)nicotinic Acid

A solution of 3-methylphenylacetonitrile (4.51 g) in dry 1,4-dioxane (30 ml) (solvent quantities are sometimes important in these reactions) was added, in one portion, to a stirred suspension of sodium hydride (60% suspension oil; 4.26 g). The resulting suspension was stirred at room temperature for 45 minutes. TDA-1 (2 drops) was added. The mixture was stirred at 80° C. for 15 minutes then at room temperature for 20 minutes.

A solution of 2-chloronicotinic acid (5.0 g) in 1,4-dioxane (70 ml) was added, in one portion, to the mixture which was then stirred at the reflux temperature for 2.75 hours.

On cooling to 80° C., the mixture was stirred vigorously while air was bubbled through for 2 hours. The reaction mixture was maintained at 65°–70° C. during the oxidation. After standing at room temperature overnight, the oxidation process was recommenced and continued, as described above, for a further 2 hours.

The mixture was allowed to cool to room temperature and was then carefully quenched by the dropwise addition of water (with continuous stirring). The resulting mixture was washed with diethyl ether then acidified to pH 3 with 2N hydrochloric acid. The mixture was extracted with ethyl acetate. The organic phases were combined, washed with water, dried and evaporated.

The crude product was triturated with hexane to yield the title compound as a yellow solid, 5.33 g, m.p. 184°–189° C.

By proceeding in a similar manner, the following compounds of general formula II were prepared:
(i) 2-(3-Cyanobenzoyl)-5-methylnicotinic acid (not isolated);
(ii) 5-Propyl-2-(3-trifluoromethylbenzoyl)nicotinic acid m.p. 155°–159° C.

Reference Example 3

The preparation of 2-chloro-5-methylnicotinic acid

An aqueous solution of sodium hydroxide (9.2 g) was added to an ice-cooled, stirred solution of methyl 2-chloro-5-methylnicotinoate (35.28 g) in methanol at such a rate so that the temperature of the reaction mixture did not exceed 30° C.

The mixture was then stirred at room temperature for 1.5 hours. Solvent was evaporated. The residue was diluted with water and acidified to pH 2 with concentrated hydrochloric acid. The precipitate was collected by filtration, washed with water and dried to yield the title compound as a pale yellow solid, 31.92 g, m.p. 180°–180.5° C.

Reference Example 4

The preparation of methyl 2-chloro-5-methylnicotinoate

Hydrogen chloride gas was bubbled through a suspension of methyl 5-(N,N-dimethylamino)-2-cyano-4-methylpent-2,4-dienoate (37.4 g) in 1,2-dichloroethane for 6 hours. Further saturation of the suspension with HCl gas was followed by stirring at room temperature overnight.

Excess HCl was blown out of the reaction mixture with nitrogen gas. The mixture was washed with water, dried and evaporated. The resulting oil crystallised on standing to yield the title compound as orange crystals, 35.28 g. NMR(CDCl$_3$) d=2.25 (s,3H,CH$_3$), 3.85(s,3H,CO$_2$CH$_3$), 7.85 (d,1H), 8.23 (d,1H).

Reference Example 5

The preparation of methyl 5-(N,N-dimethylamino)-2-cyano-4-methylpent-2,4-dienoate A solution of oxalyl chloride (83.2 g) in 1,2-dichloroethane was added dropwise to a stirred, cooled (0° C.) solution of dimethylformamide (109.5 g) in 1,2-dichloroethane so that the temperature of the reaction mixture did not exceed 10° C. The resulting mixture was stirred at 0°–5° C. for a further 1.75 hours then allowed to reach room temperature.

2-Methylmalonic acid (35.4 g) was added to the stirred mixture. When gas evolution had ceased, the mixture was stirred at the reflux temperature for 6 hours then at room temperature overnight.

Solvent was evaporated (keeping both temperature at 25° C. or less) and replaced with dry methanol. Methyl cyanoacetate (32.7 g) was added and the mixture was stirred. Sodium methoxide (53.5 g) was then added ensuring that the reaction mixture temperature did not exceed 30° C. The cooled mixture was stirred for a further 30 minutes then at room temperature for 3.5 hours.

Solvent was removed by evaporation and replaced with dichloromethane. The mixture was then washed with water, dried and evaporated. The crude product was triturated with cold methanol to yield the title compound as a yellow crystalline solid, 37.44 g, m.p. 167.5°–168.5° C.

Reference Example 6

The preparation of 2-chloro-6-methylnicotinic acid

Phosphorus oxychloride (50 ml) was added with cooling (icebath) to 2-hydroxy-6-methylnicotinic acid (10 g) over a period of 20 minutes.

The resulting suspension was stirred at the reflux temperature for 4 hours to give an orange solution. The excess phosphorus oxychloride was removed by evaporation. The residue was added carefully to ice/water with stirring. The mixture was basified to pH 10 with 2N sodium hydroxide solution then stirred for 1 hour. The resulting solution was washed with diethyl ether then acidified to pH 3–4 with concentrated hydrochloric acid. The mixture was extracted with ethyl acetate. The organic extracts were combined, dried and evaporated to yield the title compound as a yellow solid, 4.63 g, m.p. 161°–162° C.

Further acidification of the aqueous residue to pH 2 followed by extraction with ethyl acetate as described above yielded a further batch of the title compound as a cream solid, 5.81 g, m.p. 162°–163° C.

Reference Example 7

The preparation of 3-(methylthio)phenylacetonitrile

A solution of 3-aminophenylacetonitrile (0.87 g) in chloroform was added to dimethyldisulphide (6.93 g) to give a yellow solution. tert-Butyl nitrite (90%; 0.74 g) was then added and the mixture was stirred at 60° C. until the reaction had initiated. At this point, the heat source was removed.

A small amount of a solution of 3-aminophenylacetonitrile (4 g) in chloroform was added to the above mixture followed by a small amount of a solution of tert-butyl nitrite (3.47 g) in chloroform at 50°-60° C.

The mixture was then stirred at room temperature for 30 minutes and then heated to 55° C. Dimethyl disulphide (5.67 g) was then added followed by the alternate addition of a solution of 3-aminophenylacetonitrile (4 g) in chloroform and a solution of tert-butylnitrite (3.46 g) in chloroform maintaining the reaction temperature at 50°-53° C. The mixture was then stirred at room temperature for 3 hours.

Water was added to the resulting brown solution. The mixture was mixed thoroughly and the layers were separated. The organic layer was washed successively with water, 2N hydrochloric acid then water, dried and evaporated. The crude product (14.09 g) was purified by column chromatography to yield the title compound as an orange oil, 3.32 g. NMR data (CDCl$_3$) d=2.48 (s,3H, SCH$_3$), 3.7 (s,2H), 7.05–7.5 (m,4H).

Reference Example 8

The preparation of 3-aminophenylacetonitrile

3-Nitrophenylacetonitrile (28 g) was added to a suspension of tin (II) chloride dihydrate (117.3 g) in concentrated hydrochloric acid. An exotherm of 20° C. was observed and was controlled at this level by occasional ice cooling. The resulting mixture was stirred at 35°-40° C. with occasional cooling for 15 minutes and then at room temperature for 4 hours.

The reaction mixture was allowed to stand at room temperature overnight.

The mixture was poured carefully into ice/water which was then basified to pH 9 with 2N sodium hydroxide solution, ensuring that the temperature did not exceed 30° C. The mixture was extracted with diethyl ether. The organic extracts were combined, washed with water, dried and evaporated.

The crude product (22.2 g) was distilled under reduced pressure to give an orange oil, 16.13 g, b.p. 129°-134° C. at 1.5 mmHg.

The product was futher purified by column chromatography to yield the title compound as a yellow oil, 11.36 g.

NMR (DMSO-D$_6$) d=3.83 (s,2H), 5.22 (br.s.,2H), 6.37–6.65 (m, 3H), 6.96–7.1 (m,1H).

It is to be understood that in the following description references to compounds of general formula I are to such compounds as hereinbefore defined but including compounds wherein R, R$^1$ and R$^2$ simultaneously represent hydrogen.

According to a feature of the present invention, there is provided a method for controlling the growth of weeds (i.e. undesired vegetation) at a locus which comprises applying to the locus a herbicidally effective mount of at least one pyrido[2,3-d]pyridazin-5-one or pyridazin-5-thione derivative of general formula (I) or an agriculturally acceptable salt thereof. For this purpose, the pyrido[2,3-d]pyridazin-5-one or pyridazin-5-thione derivatives are normally used in the form of herbicidal compositions (i.e. in association with compatible diluents or carriers and/or surface active agents suitable for use in herbicidal compositions), for example as hereinafter described.

The compounds of general formula (I) show herbicidal activity against dicotyledonous (i.e. broad-leafed) and monocotyledonous (e.g. grass) weeds by pre- and-/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of general formula (I) may be used to control the growth of:

broad-leafed weeds, for example, *Abutilon theophrasti, Amaranthus retroflexus, Bidens pilosa, Chenopodium album, Galium aparine,* Ipomoea spp. e.g. *Ipomoea purpurea, Sesbania exaltata, Sinapis arvensis, Solanum nigrum* and *Xanthium strumarium,* and grass weeds, for example *Alopecurus myosuroides, Avena fatua, Digitaria sanguinalis, Echinochloa crusgalli, Eleusine indica* and Setaria spp, e.g. *Setaria faberii* or *Setaria viridis,* and sedges, for example, *Cyperus esculentus.*

The amounts of compounds of general formula (I) applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 5 kg of active material per hectare give good results. However, it is to be understood that higher or lower application rates may be used, depending upon the particular problem of weed control encountered.

The compounds of general formula (I) may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 0.01 kg and 4.0 kg, and preferably between 0.01 kg and 2.0 kg, of active material per hectare are particularly suitable.

The compounds of general formula (I) may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 5.0 kg, and preferably between 0.5 kg and 4.0 kg of active material per hectare.

The compounds of general formula (I) may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 1.0 kg and 20.0 kg, and preferably between 5.0 and 10.0 kg, of active material per hectare are particularly suitable for this purpose.

When used to control the growth of weeds by pre-emergence application, the compounds of general formula (I) may be incorporated into the soil in which the weeds are expected to emerge. It will be appreciated that when the compounds of general formula (I) are used to control the growth of weeds by post-emergence application, i.e. by application to the aerial or exposed portions of emerged weeds, the compounds of general formula (I) will also normally come into contact with the soil and may also then exercise a pre-emergence control on later-germinating weeds in the soil.

Where especially prolonged weed control is required, the application of the compounds of general formula (I) may be repeated if required.

According to a further feature of the present invention, there are provided compositions suitable for herbicidal use comprising one or more of the pyrido[2,3-d]pyridazin-5-one or pyridazin-5-thione derivatives of general formula I or an agriculturally acceptable salt thereof, in association with, and preferably homogeneously dispersed in, one or more compatible agriculturally-acceptable diluents or carriers and/or surface active agents [i.e. diluents or carriers and/or surface active agents of the type generally accepted in the an as being suitable for use in herbicidal compositions and which are compatible with compounds of general formula (I)]. The term "homogeneously dispersed" is used to include compositions in which the compounds of general formula (I) are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of general formula (I).

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, talc, calcined magnesia, kieselguhr, tricalcium phosphate, powdered cork, absorbent carbon black and clays such as kaolin and bentonite. The solid compositions (which may take the form of dusts, granules or wettable powders) are preferably prepared by grinding the compounds of general formula (I) with solid diluents or by impregnating the solid diluents or carriers with solutions of the compounds of general formula (I) in volatile solvents, evaporating the solvents and, if necessary, grinding the products so as to obtain powders. Granular formulations may be prepared by absorbing the compounds of general formula (I) (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of general formula (I) may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Unless otherwise specified, the following percentages are by weight. Preferred herbicidal compositions according to the present invention are aqueous suspension concentrates which comprise from 10 to 70% of one or more compounds of general formula (I), from 2 to 10% of surface-active agent, from 0.1 to 5% of thickener and from 15 to 87.9% of water;

wettable powders which comprise from 10 to 90% of one or more compounds of general formula (I), from 2 to 10% of surface-active agent and from 8 to 88% of solid diluent or carrier;

water soluble or water dispersible powders which comprise from 10 to 90% of one or more compounds of general formula (I), from 2 to 40% of sodium carbonate and from 0 to 88% of solid diluent;

liquid water soluble concentrates which comprise from 5 to 50%, e.g. 10 to 30%, of one or more compounds of general formula (I), from 5 to 25% of surface-active agent and from 25 to 90%, e.g. 45 to 85%, of water miscible solvent, e.g. dimethylformamide, or a mixture of water-miscible solvent and water, liquid emulsifiable suspension concentrates which comprise from 10 to 70% of one or more compounds of general formula (I), from 5 to 15% of surface-active agent, from 0.1 to 5% of thickener and from 10 to 84.9% of organic solvent;

granules which comprise from 1 to 90%, e.g. 2 to 10% of one or more compounds of general formula (I), from 0.5 to 7%, e.g. 0.5 to 2%, of surface-active agent and from 3 to 98.5%, e.g. 88 to 97.5%, of granular carrier and emulsifiable concentrates which comprise 0.05 to 90%, and preferably from 1 to 60% of one or more compounds of general formula (I), from 0.01 to 10%, and preferably from 1 to 10%, of surface-active agent and from 9.99 to 99.94%, and preferably from 39 to 98.99%, of organic solvent.

Herbicidal compositions according to the present invention may also comprise the compounds of general formula (I) in association with, and preferably homogeneously dispersed in, one or more other pesticidally active compounds and, if desired, one, or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine [2-chloro-4-ethylamino-6-isopropylamino-1,3,5-triazine], bromoxynil [3,5-dibromo-4-hydroxybenzonitrile], chlortoluron [N'-(3-chloro-4-methylphenyl)-N,N-dimethylurea], cyanazine [2-chloro-4-(1-cyano-1-methylethylamino)-6-ethylamino-1,3,5-triazine], 2,4-D [2,4-dichlorophenoxy-acetic acid], dicamba [3,6-dichloro-2-methoxybenzoic acid], difenzoquat [1,2-dimethyl-3,5-diphenyl-pyrazolium salts], flampropmethyl [methyl N-2-(N-benzoyl-3-chloro-4-fluoroanilino)-propionate], fluometuron [N'-(3-trifluoro-methylphenyl)-N,N-dimethylurea], isoproturon [N'-(4-isopropylphenyl)-N,N-dimethylurea], nicosulfuron [2-(4,6-dimethoxypyrimidin-2-ylcarbamoylsulfamoyl)-N,N-dimethylnicotinamide], insecticides, e.g. synthetic pyrethroids, e.g. permethrin and cypermethrin, and fungicides, e.g. carbamates, e.g. methyl N-(1-butyl-carbamoyl-benzimidazol-2-yl)carbamate, and triazoles e.g. 1-(4-chloro-phenoxy)-3,3-dimethyl-1-(1,2,4-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the pyrido[2,3-d]pyridazin-5-one or pyridazin-5-thione derivatives of general formula (I) or, as is preferred, a herbicidal composition as hereinbefore described, and preferably a herbicidal concentrate which must be diluted before use, comprising at least one of the pyrido[2,3-d]pyridazin-5-one or pyridazin-5-thione derivatives of general formula (I) within a container for the aforesaid derivative or derivatives of general formula (I), or a said herbicidal composition, and instructions physically associated with the aforesaid container setting out the manner in which the aforesaid derivative or derivatives of general formula (I) or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drams of metal, which may be internally lacquered, and plastics materials, bottles or glass and plastics materials and, when the contents of the container is a solid, for example granular, herbicidal compositions, boxes, for example of cardboard, plastics materials and metal, or sacks. The containers will normally be of sufficient capacity to contain amounts of the pyrido[2,3-d]pyridazin-5-one or pyridazin-5-thione derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 20 kg of active material per hectare in the manner and for the purposes hereinbefore described.

The following Examples illustrate herbicidal compositions according to the present invention:

EXAMPLE C1

A soluble concentrate is formed from:

| | |
|---|---|
| Active ingredient (compound 1) | 20% w/v |
| Potassium hydroxide solution 33% w/v | 10% v/v |
| Tetrahydrofurfuryl alcohol (THFA) | 10% v/v |
| Water | to 100 volumes. | by stirring THFA, active ingredient (compound 1) and 90% volume of water and slowly adding the potassium hydroxide solution until a steady pH 7–8 was obtained then making up to volume with water.

Similar soluble concentrates may be prepared as described above by replacing the pyrido[2,3-d]pyridazin-5-one (compound 1) with other compounds of general formula (I).

EXAMPLE C2

A wettable powder is formed from:

| | |
|---|---|
| Active ingredient (compound 1) | 50% w/w |
| Sodium dodecylbenzene sulphonate | 3% w/w |
| Sodium lignosulphate | 5% w/w |
| Sodium formaldehyde alkylnaphthalene sulphonate | 2% w/w |
| Microfine silicon dioxide | 3% w/w and |
| China clay | 37% w/w | by blending the above ingredients together and grinding the mixture in an air jet mill.

Similar wettable powders may be prepared as described above by replacing the pyrido[2,3-d]pyridazin-5-one (compound 1) with other compounds of general formula (I).

EXAMPLE C3

A water soluble powder is formed from:

| | |
|---|---|
| Active ingredient (compound 1) | 50% w/w |
| Sodium dodecylbenzenesulphonate | 1% w/w |
| Microfine silicon dioxide | 2% w/w |
| Sodium bicarbonate | 47% w/w | by mixing the above ingredients and grinding the above mixture in a hammer mill.

Similar water soluble powders may be prepared as described above by replacing the pyrido[2,3-d]pyridazin-5-one (compound 1) with other compounds of general formula (I).

Representative compounds of general formula (I) have been used in herbicidal applications according to the following procedures.

METHOD OF USE OF HERBICIDAL COMPOUNDS;

a) General

Appropriate quantities of the compounds used to treat the plants were dissolved in acetone to give solutions equivalent to application rates of up to 4000 g test compound per hectare (g/ha). These solutions were applied from a standard laboratory herbicide sprayer delivering the equivalent of 290 liters of spray fluid per hectare.

b) Weed control: Pre-emergence

The seeds were sown in 70 mm square, 75 mm deep plastic pots in non-sterile soil. The quantities of seed per pot were as follows:

| Weed species | | Approx number of seeds/pot |
|---|---|---|
| 1) | Broad-leafed weeds | |
| | Abutilon theophrasti | 10 |
| | Amaranthus retroflexus | 20 |
| | Galium aparine | 10 |
| | Ipomoea purpurea | 10 |
| | Sinapis arvensis | 15 |
| | Xanthium strumarium | 2. |
| 2) | Grass weeds | |
| | Alopecurus myosuroides | 15 |
| | Avena fatua | 10 |
| | Echinochloa crus-galli | 15 |
| | Setaria viridis | 20. |
| 3) | Sedges | |
| | Cyperus esculentus | 3. |
| Crop | | |
| 1) | Broad-leafed | |
| | Cotton | 3 |
| | Soya | 3. |
| 2) | Grass | |
| | Maize | 2 |
| | Rice | 6 |
| | Wheat | 6. |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed control: Post-emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

1) Broad leafed weeds

| Weed Species | Number of Plants per pot | Growth stage |
|---|---|---|
| Abutilon theophrasti | 3 | 1–2 leaves |
| Amaranthus retroflexus | 4 | 1–2 leaves |
| Galium aparine | 3 | 1st whorl |
| Ipomoea purpurea | 3 | 1–2 leaves |
| Sinapis arvensis | 4 | 2 leaves |
| Xanthium strumarium | 1 | 2–3 leaves. |

2) Grass weeds

| Weed Species | Number of plants per pot | Growth stage |
|---|---|---|
| Alopecurus myosuroides | 8–12 | 1–2 leaves |
| Avena fatua | 12–18 | 1–2 leaves |
| Echinochloa crus-galli | 4 | 2–3 leaves |
| Setaria viridis | 15–25 | 1–2 leaves. |

3) Sedges

| Weed Species | Number of plants per pot | Growth stage |
|---|---|---|
| Cyperus esculentus | 3 | 3 leaves. |

1) Broad leafed

| Crops | Number of plants per pot | Growth stage |
|---|---|---|
| Cotton | 2 | 1 leaf |
| Soya | 2 | 2 leaves. |

2) Grass

| Crops | Number of plants per pot | Growth stage |
|---|---|---|
| Maize | 2 | 2-3 leaves |
| Rice | 4 | 2-3 leaves |
| Wheat | 5 | 2-3 leaves. |

The compounds used to treat the pints were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20-24 days after spraying. The results were expressed as the percentage reduction in growth or damage to the crop or weeds, in comparison with the plants in the control pots. When applied at 4000 g/hectare pre- or post-emergence, compounds 2, 3, 4, 10-13, 15-23, 25, 27-29, 31 and 34 gave at least 90% reduction in growth of one or more weed species.

When applied at 2000 g/hectare pre- or post-emergence, compounds 8 and 9 gave at least 90% reduction in growth of one or more weed species.

When applied at 1000 g/hectare pre- or post-emergence, compounds 1, 5-7, 14, 33 and 35-46 gave at least 90% reduction in growth of one or more weed species.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A method for controlling the growth of weeds at a locus comprising applying to said locus a herbicidally effective amount of a compound of the formula:

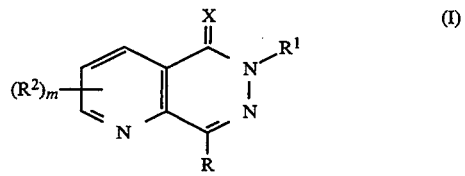

(I)

wherein:
R and $R^1$, which can be the same or different, each represent phenyl optionally substituted by from 1 to 5 groups $R^3$, which can be the same or different;

$R^2$ represents:
halogen;
straight- or branched-chain alkyl, alkenyl or alkynyl having up to six carbons, optionally substituted by one or more halogen;
—CN; —CO$_2$R$^4$; —S(O)$_r$R$^4$; —NO$_2$; —NR$^{41}$R$^{42}$; —OH; —COR$^4$; —S(O)$_r$R$^5$; —CO$_2$R$^5$; —OR$^5$; —CONR$^{41}$R$^{42}$; —OSO$_2$R$^5$; —OSO$_2$R$^6$; —OCH$_2$R$^5$; —N(R$^{41}$)COR$^6$; —N(R$^{41}$)SO$_2$R$^5$; —N(R$^{41}$)SO$_2$R$^6$; —SO$_2$NR$^{41}$R$^{42}$;
phenyl optionally substituted by from one to five groups $R^3$; or
straight- or branched-chain alkoxy having up to six carbons, optionally substituted by one or more halogen;

X represents oxygen or sulphur;
$R^3$ represents:
halogen;
straight- or branched-chain alkoxy having up to six carbons, optionally substituted by one or more halogen;
straight- or branched-chain alkyl, alkenyl or alkynyl having up to six carbons, optionally substituted by one or more halogen;
—OH; —S(O)$_r$R$^4$; —CO$_2$R$^4$; —COR$^4$; —CN; —NO$_2$; —NR$^{41}$R$^{42}$; —S(O)$_r$R$^5$; —CO$_2$R$^5$; —OR$^5$; —CONR$^{41}$R$^{42}$; —OSO$_2$R$^5$; —OSO$_2$R$^6$; —OCH$_2$R$^5$; —N(R$^{41}$)COR$^6$; —N(R$^{41}$)SO$_2$R$^5$; —N(R$^{41}$)SO$_2$R$^6$; or —SO$_2$NR$^{41}$R$^{42}$;

$R^4$ represents hydrogen or straight- or branched-chain alkyl having up to six carbons, optionally substituted by one or more halogen;
$R^{41}$ and $R^{42}$, which can be the same or different, each represent hydrogen or straight- or branched-chain alkyl having up to four carbons, optionally substituted by one or more halogen;
$R^5$ represents phenyl, optionally bearing from one to five substituents selected from the group consisting of halogen, nitro, cyano, $R^4$ and —OR$^4$;
$R^6$ represents straight- or branched-chain alkyl having up to six carbons, optionally substituted by one or more halogen;
m represents zero or an integer from one to three; when m is greater than one, the groups $R^2$ can be the same or different; and
r represents zero, one or two;
or an agriculturally acceptable salt thereof.

2. The method according to claim 1 wherein X represents oxygen.

3. The method according to claim 1 wherein R and $R^1$, which can be the same or different, each represent phenyl which is unsubstituted, monosubstituted in the 3- or 4-position by a group $R^3$, or disubstituted in the 2- and 4-positions or in the 3- and 4-positions by two groups $R^3$, which can be the same or different.

4. The method according to claim 1 wherein R and $R^1$, which can be the same or different, each represent phenyl which is unsubstituted, monosubstituted in the 3- or 4-position by a group $R^3$, or disubstituted in the 2- and 4-positions by two groups $R^3$, which can be the same or different.

5. The method according to claim 1 wherein R and $R^1$, which can be the same or different, each represent phenyl which is disubstituted in the 3- and 4-positions by two groups $R^3$.

6. The method according to claim 4 wherein m represents zero.

7. The method according to claim 4 wherein X represents oxygen.

8. The method according to claim 4 wherein m represents zero and X represents oxygen.

9. The method according to claim 4 wherein $R^2$ represents straight- or branched-chain alkyl having up to six carbons.

10. The method according to claim 4 wherein the 3-position of the pyrido[2,3-d]pyridazin-5-one or 5-thione ring system is substituted by a group $R^2$.

11. The method according to claim 10 wherein $R^2$ represents straight- or branched-chain alkyl having up to six carbons.

12. The method according to claim 1 wherein the compound is:

6,8-diphenylpyrido[2,3-d]pyridazin-5-one;
6-phenyl-8-(3-trifluoromethylphenyl)pyrido[2,3-d]pyridazin-5-one;
6-(4-fluorophenyl)-8-(3-trifluoromethylphenyl)pyrido[2,3-d]pyridazin-5-one;
6-(2,4-difluorophenyl)-8-(3-trifluoromethylphenyl)pyrido[2,3-d]pyridazin-5-one;
6-(4-fluorophenyl)-8-(3-methoxyphenyl)pyrido[2,3-d]pyridazin-5-one;
6-(4-methoxyphenyl)-8-(3-trifluoromethylphenyl)pyrido[2,3-d]pyridazin-5-one;
6-(4-chlorophenyl)-8-(3-trifluoromethylphenyl)pyrido[2,3-d]pyridazin-5-one;
8-(3-chlorophenyl)-6-(4-fluorophenyl)pyrido[2,3-d]pyridazin-5-one;
6-(4-methylphenyl)-8-(3-trifluoromethylphenyl)pyrido[2,3-d]pyridazin-5-one;
8-(4-chlorophenyl)-6-(4-fluorophenyl)pyrido[2,3-d]pyridazin-5-one;
6-(4-fluorophenyl)-8-phenylpyrido[2,3-d]pyridazin-5-one;
8-(3-cyanophenyl)-6-(4-fluorophenyl)pyrido[2,3-d]pyridazin-5-one;
8-(2-chlorophenyl)-6-(4-fluorophenyl)pyrido[2,3-d]pyridazin-5-one;
6-(4-fluorophenyl)-8-(3-trifluoromethylphenyl)pyrido[2,3-d]pyridazin-5-thione;
6-(4-fluorophenyl)-3-methyl-8-(3-trifluoromethylphenyl)pyrido[2,3-d]pyridazine-5-one;
6-(3-fluorophenyl)-8-(3-trifluoromethylphenyl)pyrido[2,3-d]pyridazin-5-one;
8-(3-trifluoromethylphenyl)-6-(4-trifluoromethylphenyl)pyrido[2,3-d]pyridazin-5-one;
6-(4-fluorophenyl)-2-methyl-8-(3-trifluoromethylphenyl)pyrido[2,3-d]pyridazin-5-one;
6-(4-methanesulphonylphenyl)-8-(3-trifluoromethylphenyl)pyrido[2,3-d]pyridazin-5-one;
6-(4-bromophenyl)-8-(3-trifluoromethylphenyl)pyrido[2,3-d]pyridazin-5-one;
6-(3-methylphenyl)-8-(3-trifluoromethylphenyl)pyrido[2,3-d]pyridazin-5-one;
6-(3,4-dichlorophenyl)-8-(3-trifluoromethylphenyl)pyrido[2,3-d]pyridazin-5-one;
6-(3-cyanophenyl)-8-(3-trifluoromethylphenyl)pyrido[2,3-d]pyridazin-5-one;
6-(4-fluorophenyl)-8-(3-trifluoromethoxyphenyl)pyrido[2,3-d]pyridazin-5-one;
6-(3,4-difluorophenyl)-8-(3-trifluoromethylphenyl)pyrido[2,3-d]pyridazin-5-one;
8-(3-bromophenyl)-6-(4-fluorophenyl)pyrido[2,3-d]pyridazin-5-one;
8-(3-cyanophenyl)-6-(4-trifluoromethylphenyl)pyrido[2,3-d]pyridazin-5-one;
6-(4-chlorophenyl)-8-(3-cyanophenyl)pyrido[2,3-d]pyridazin-5-one;
6-(4-fluorophenyl)-8-[(3-methylthio)phenyl]pyrido[2,3-d]pyridazin-5-one;
6-(4-fluorophenyl)-8-(3-methanesulphonylphenyl)pyrido[2,3-d]pyridazin-5-one;
6-(4-chlorophenyl)-3-methyl-8-(3-trifluoromethylphenyl)pyrido[2,3-d]pyridazin-5-one;
3-methyl-6-(4-trifluoromethylphenyl)-8-(3-trifluoromethylphenyl)pyrido[2,3-d]pyridazin-5-one;
6-(4-chlorophenyl)-8-(3-trifluoromethoxyphenyl)pyrido[2,3-d]pyridazin-5-one;
8-(3-trifluoromethoxyphenyl)-6-(4-trifluoromethylphenyl)pyrido[2,3-d]pyridazin-5-one;
6-(4-chlorophenyl)-3-methyl-8-(3-trifluoromethoxyphenyl)pyrido[2,3-d]pyridazin-5-one;
3-methyl-8-(3-trifluoromethoxyphenyl)-6-(4-trifluoromethylphenyl)pyrido[2,3-d]pyridazin-5-one;
6-(4-fluorophenyl)-3-methyl-8-(3-trifluoromethoxyphenyl)pyrido[2,3-d]pyridazin-5-one;
8-(3-cyanophenyl)-6-(4-fluorophenyl)-3-methylpyrido[2,3-d]pyridazin-5-one;
6-(4-trifluoromethoxyphenyl)-8-(3-trifluoromethylphenyl)pyrido[2,3-d]pyridazin-5-one;
6-(3-trifluoromethylphenyl)-8-(3-trifluoromethylphenyl)pyrido[2,3-d]pyridazin-5-one;
6-(4-nitrophenyl)-8-(3-trifluoromethylphenyl)pyrido[2,3-d]pyridazin-5-one;
8-(3-cyanophenyl)-3-methyl-6-(4-trifluoromethylphenyl)pyrido[2,3-d]pyridazin-5-one;
6-(4-aminophenyl)-8-(3-trifluoromethylphenyl)pyrido[2,3-d]pyridazin-5-one;
6-(4-fluorophenyl)-8-(3-methylphenyl)pyrido[2,3-d]pyridazin-5-one;
6-(4-fluorophenyl)-3-propyl-8-(3-trifluoromethylphenyl)pyrido[2,3-d]pyridazin-5-one;
6-(2-chloro-4-trifluoromethylphenyl)-8-(3-trifluoromethylphenyl)pyrido[2,3-d]pyridazin-5-one;
6-(4-aminosulphonylphenyl)-8-(3-trifluoromethylphenyl)pyrido[2,3-d]pyridazin-5-one; or
6-(3-nitrophenyl)-8-(3-trifluoromethylphenyl)pyrido[2,3-d]pyridazin-5-one;

or an agriculturally acceptable salt thereof.

* * * * *